United States Patent
Venturini et al.

(10) Patent No.: US 10,136,921 B2
(45) Date of Patent: Nov. 27, 2018

(54) ELONGATED PIN FOR APPLICATION OF AN EXTERNAL FIXATOR

(71) Applicant: ORTHOFIX S.R.L., Bussolengo (Verona) (IT)

(72) Inventors: Daniele Venturini, Povegliano Veronese (IT); Andrea Ottoboni, Rovigo (IT); Enrico Zandona', Verona (IT); Michele Coati, San Pietro in Cariano (IT)

(73) Assignee: Orthofix S.R.L., Verona (IT)

(*) Notice: Subject to any disclaimer, the term of this patent is extended or adjusted under 35 U.S.C. 154(b) by 0 days.

(21) Appl. No.: 15/113,642

(22) PCT Filed: Jan. 22, 2015

(86) PCT No.: PCT/EP2015/200118
§ 371 (c)(1),
(2) Date: Jul. 22, 2016

(87) PCT Pub. No.: WO2015/110266
PCT Pub. Date: Jul. 30, 2015

(65) Prior Publication Data
US 2017/0209176 A1 Jul. 27, 2017

(30) Foreign Application Priority Data
Jan. 24, 2014 (IT) .............................. MI2014A0094

(51) Int. Cl.
*A61B 17/84* (2006.01)
*A61B 17/64* (2006.01)
(Continued)

(52) U.S. Cl.
CPC .......... *A61B 17/6458* (2013.01); *A61B 17/60* (2013.01); *A61B 17/846* (2013.01);
(Continued)

(58) Field of Classification Search
CPC ... A61B 17/60–17/6491; A61B 17/84–17/848; A61B 17/86–17/8695
(Continued)

(56) References Cited

U.S. PATENT DOCUMENTS

| 5,443,464 A | 8/1995 | Russell et al. |
| 2005/0085754 A1 | 4/2005 | Werding et al. |

(Continued)

FOREIGN PATENT DOCUMENTS

| EP | 1284666 B1 | 1/2007 |
| EP | 2319436 B1 | 2/2013 |

OTHER PUBLICATIONS

International Search Report and Written Opinion, PCT/EP2015/000118, dated Apr. 29, 2015, 8 pages.

*Primary Examiner* — Nicholas Plionis
(74) *Attorney, Agent, or Firm* — Baker & McKenzie LLP

(57) ABSTRACT

Elongated pin (1) for an external fixator for temporary and/or permanent fixation applications to treat bone fractures and to connect two or more bone fragments to each other, comprising an elongated cylindrical stem (2) extending along a longitudinal axis (X) and a conical end portion (3) with a tip and an external thread for inserting the pin (1) into a bone, wherein said conical end portion (3) with a tip has an overall length, measured along the longitudinal axis (X), equal to the diameter (d) of the stem (2) ±20% of said diameter (d) and wherein the stem (2) comprises a cylindrical end area (4) extending adjacent to the conical portion (3) and having an external thread which extends over a length, measured along the longitudinal axis (X), equal to the diameter (d) of the stem (2) ±25% of said diameter (d).

9 Claims, 4 Drawing Sheets

(51) Int. Cl.
*A61B 17/86* (2006.01)
*A61B 17/60* (2006.01)

(52) U.S. Cl.
CPC ........ *A61B 17/861* (2013.01); *A61B 17/8625* (2013.01); *A61B 17/8635* (2013.01); *A61B 17/6466* (2013.01); *A61B 17/848* (2013.01)

(58) Field of Classification Search
USPC .................................................... 606/53–59
See application file for complete search history.

(56) References Cited

U.S. PATENT DOCUMENTS

| | | | |
|---|---|---|---|
| 2009/0018589 A1* | 1/2009 | Smisson, III | A61B 17/863 606/301 |
| 2009/0036889 A1* | 2/2009 | Callender | A61F 5/566 606/55 |
| 2010/0211118 A1* | 8/2010 | Christen | A61B 17/863 606/312 |
| 2011/0125198 A1 | 5/2011 | Griffin | |
| 2011/0264149 A1 | 10/2011 | Pappalardo et al. | |

\* cited by examiner

ELONGATED PIN FOR APPLICATION OF AN EXTERNAL FIXATOR

TECHNICAL FIELD

The present invention relates to an elongated pin for an external fixator having the function of a monocortical pin.

PRIOR ART

External fixation systems are widely used to treat bone fractures and to connect two or more bone fragments together. Known systems use bone screws, screws and/or wires which are inserted inside the bones and which use external structural elements as fixing clamps, fixing bars or annular bars to ensure a rigid structure which keeps the bone fragments stationary and therefore allows permanent healing by means of an external fixator or by means of internal stabilization systems such endomedullary plates or nails.

In some types of treatment, particular local conditions in the fracture zone may occasionally preclude the use of permanent fixators, or the fracture may be present along with other fractures due to an injury which requires fairly lengthy surgical treatment before a permanent internal fixation system may be used.

In these cases also, some or all the fractures may be treated with external fixation systems which are specifically designed for temporary fixing and which therefore may be regarded as temporary systems, as for example described in EP 2,319,436 in the name of the same Applicant.

In any case it is very important that, at the end of treatment, each fracture is contained in a stable manner.

In this technical sector there are also many fixing systems which are used mainly as permanent fixing systems for allowing bone fractures to heal, such as the system described in EP 1,284,666 in the name of the same Applicant.

In general the temporary fixing systems are lighter and simpler, but are also less stable compared to the known permanent external fixation systems. Moreover, temporary and permanent external fixation systems may often differ in terms of the form and structure of the respective clamps.

Still in general terms, permanent external fixation systems offer a high degree of rigidity and stability for managing the lateral flexural forces and twisting torque during treatment.

Such rigidity and stability are derived partly from the alignment of the bars of the fixator along the longitudinal axis of the bone which is treated, partly from the intrinsic rigidity of the system and partly from the number of screws used.

It would be highly desirable to have the possibility of using an external fixator which combines the characteristics of simplicity and lightness of a temporary fixing system and the robustness and stability characteristics of a permanent fixing system, which damages as little as possible the bone structure so as not to adversely affect the definitive internal or external stabilization, but hitherto all the methods known from the known solutions have not produced satisfactory results.

The technical problem of the present invention is that of providing an elongated pin for an external fixator which is able to ensure stable and robust fixing of the bone fragments and which affects as little as possible the bone structure in order to avoid subsequent infection and stabilization problems, while at the same time keeping the entire system extremely light and also ensuring easy application for the surgeon.

Another object of the present invention is to provide an elongated pin for a fixing system which may be inserted in the bone without the use of conventional bone screws, which allows the gripping action to be limited to the cortical portion alone of the fractured bone in the zone where there is a cortical bone of certain thickness and which at the same is able to ensure a good grip also in the spongy bone.

SUMMARY OF THE INVENTION

These objects are achieved by an elongated pin for an external fixator, in accordance with claim 1 of the present invention.

The dependent claims define preferred and particularly advantageous embodiments of the elongated pin according to the invention.

Further characteristic features and advantages will emerge more clearly from the detailed description provided hereinbelow of a preferred, but not exclusive embodiment of the present invention, with reference to the attached figures, provided by way of a non-limiting example.

DETAILED DESCRIPTION

Figure 1:
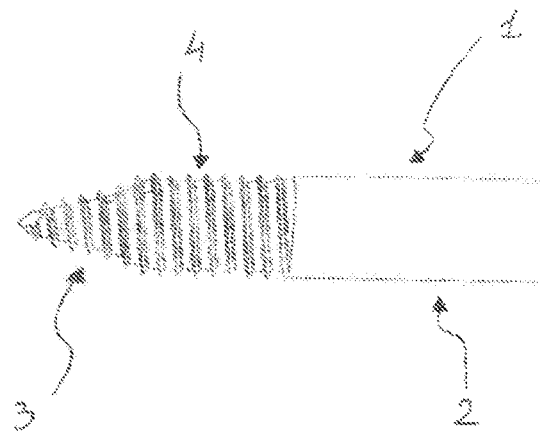
FIGS. 1 to 3 show various views of the tip of an elongated pin for an external fixator in accordance with the present invention.
Figure 2:
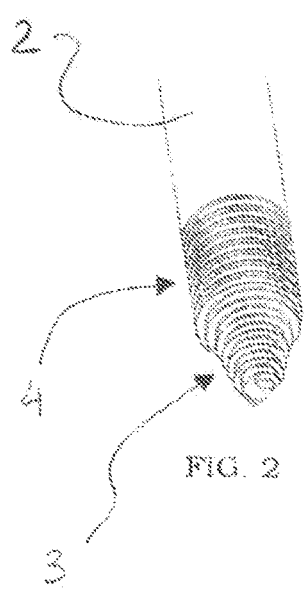
Figure 3:
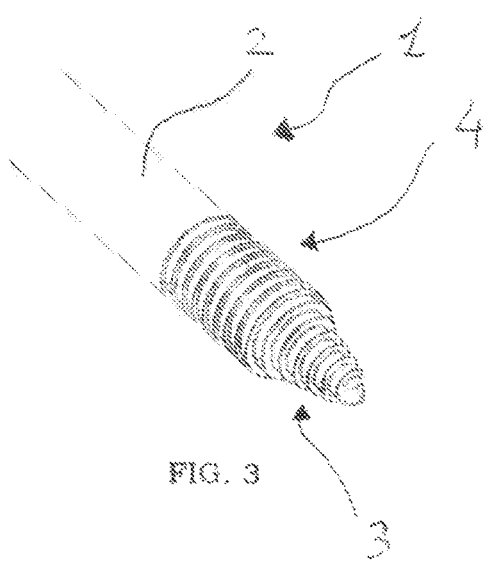
Figure 4:
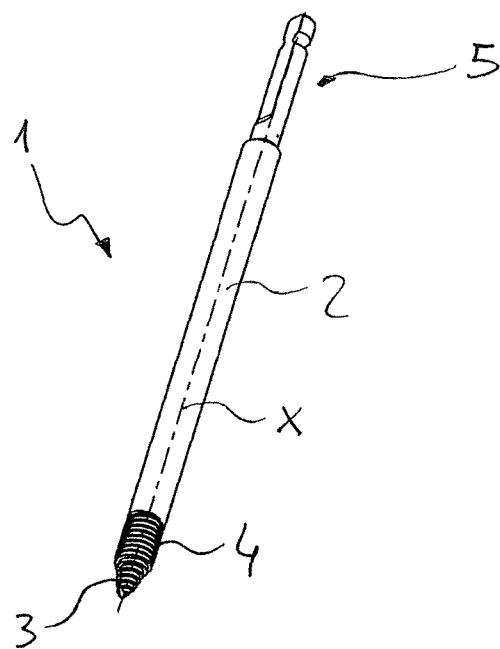
FIG. 4 shows a perspective view of the elongated pin.

With reference to the attached figures, the reference number 1 indicates overall an elongated pin comprising an elongated cylindrical stem 2 extending along a longitudinal axis X and a conical end portion 3 with a tip and an external thread for inserting the pin 1 into a bone.

In accordance with the present invention said conical end portion 3 with a tip has an overall length, measured along the longitudinal axis X, equal to the diameter d of the stem ±20% of said diameter d. Preferably, the length of the conical tip end portion 3 of the pin 1 is equal to the length of the diameter of the stem ±10% of said diameter and more preferably is equal to the length of the diameter of the stem ±5% of said diameter.

Essentially, the length of the conical threaded end portion 3 of the pin extends over a smaller distance so as to allow insertion thereof only into the cortical portion of the bone without penetrating into the medullary cavity.

In other words, the elongated pin 1 may be defined as being a "monocortical pin".

In accordance with the present invention, the stem 2 has a cylindrical end area 4 extending adjacent to the conical portion 3. This cylindrical end area of the stem has an external thread which extends over a length, measured along the longitudinal axis X, equal to the diameter d of the stem ±25% of said diameter d.

Preferably, the length of the threaded cylindrical end area 4 is equal to the length of the diameter of the stem ±20% of the length of said diameter and more preferably is equal to the length of the diameter of the stem ±10% of said diameter.

Essentially, the stem has an external thread in the end zone 4 continuous with the thread of the conical portion 3. This thread on the stem 2 adjacent to the thread of the conical portion 3 allows a good grip to be achieved also in the spongy bone.

The pin according to the present invention could be defined as being a monocortical pin with the thread which extends partially along the stem.

The spongy bone, unlike the cortical bone, does not have a strength sufficient to allow stabilization with only the conical end and therefore requires a larger gripping volume in order to ensure the necessary stability comparable with the gripping action on the cortical bone.

This stability is obtained by fully exploiting the compression and the profile of the monocortical tip which enters into the spongy bone without removal of bone material.

The spongy bone is compressed over a length such as not to be excessively invasive for the subsequent application of a nail or a plate.

The gripping performance of the elongated pin 1 according to the present invention is sufficient to ensure a stability equivalent to a bicortical pin inserted in spongy bone with a length of the threaded area 5-10 mm greater than the length of the threaded area which can be used with the pin according to the present invention.

In order to guarantee better the penetration of the pin, preferably the thread on the conical end portion 3 and the thread on the cylindrical end area 4 of the stem 2 are formed continuously; basically there are no interruptions in the thread crest.

The diameter of the stem 2 may be between 3 mm and 6.0 mm depending on the application. Preferred diameters of the stem are 3 mm, 4 mm, 5 mm and 6 mm.

The length of the elongated pin 1 may range from 50 mm to 180 mm depending on the requirements of its particular application and the dimensions of the shank.

With reference to the figures, the length of the pin is equal to 115 mm, the length of the threaded conical end portion 3 is equal to 7 mm, with a diameter d of the stem of 6 mm and length of the threaded end area 4 of the stem equal to 8 mm.

Therefore the overall thread of the end area 4 of the stem 2 and conical portion 3 is equal to 15 mm.

Figure 5:
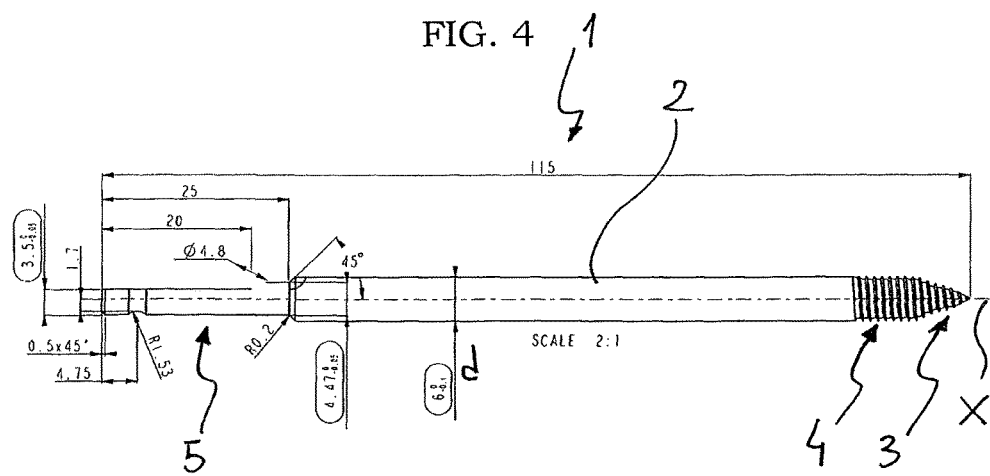
FIG. 5 shows a plan view of the elongated pin according to FIG. 4.
Figure 6:
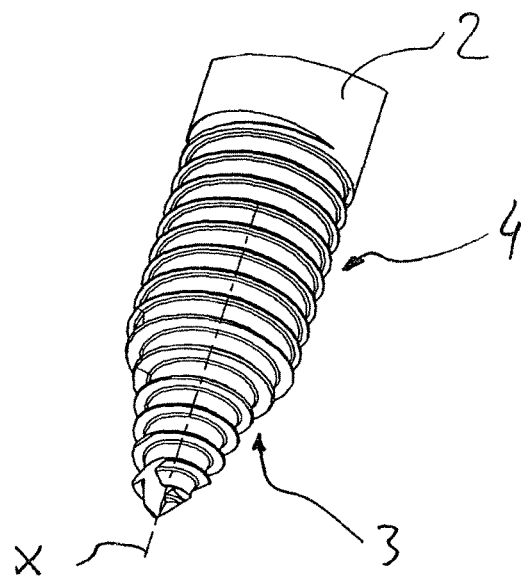
FIGS. 6 and 7 show a respective detailed view of the tip of the pin according to FIG. 4.
Figure 7:
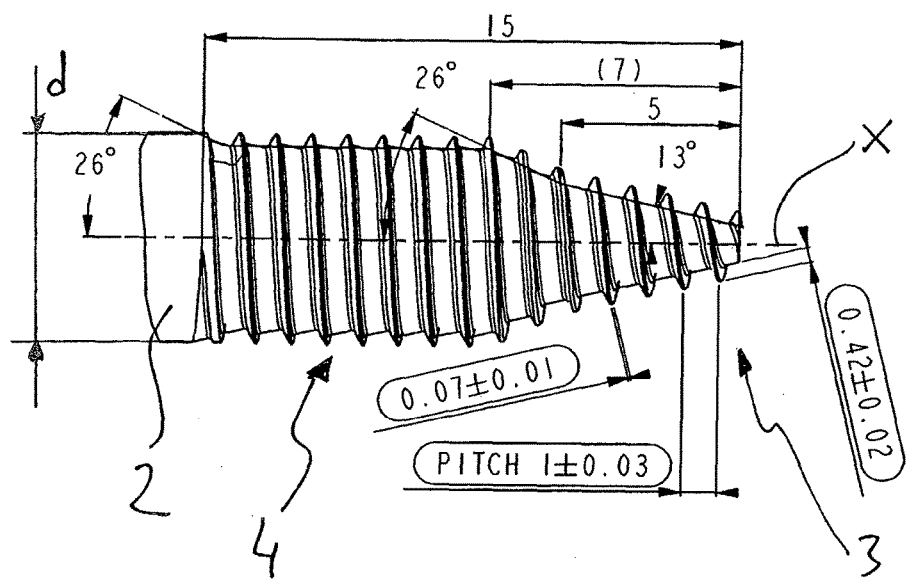

The numerical values indicated in FIGS. 5 and 7 are to be understood as being in millimeters.

As is clear, the elongated pin 1 according to the present invention has a particularly thin appearance owing to the smaller diameter.

Preferably the pin 1 is made of stainless steel with a relatively high modulus of elasticity which provides the stem 2 with a predetermined rigidity and at the same time the threaded conical end 3 with a good strength.

The threaded conical end portion 3 is of the self-drilling and self-tapping type.

In order to allow better handling of the pin 1, the profile of the end 5 opposite to the stem tip is shaped so as to allow engagement of a spanner or be inserted inside a drill to allow drilling of the bone.

Figure 8:
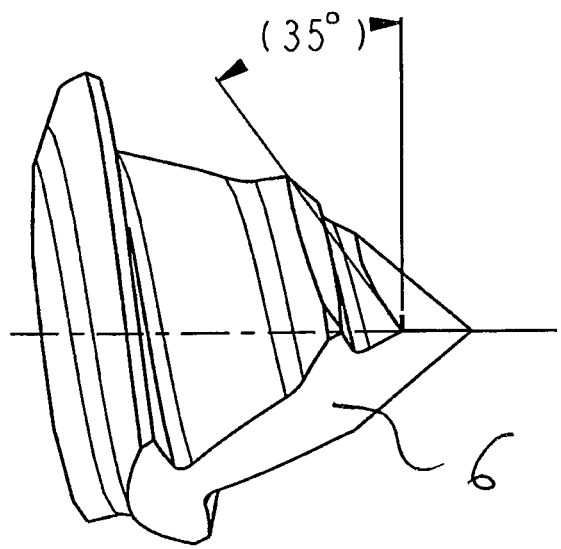
FIGS. 8 and 9 show in detail two pins with different angles of the tip of the pin in accordance with a preferred embodiment of the present invention.
Figure 9:
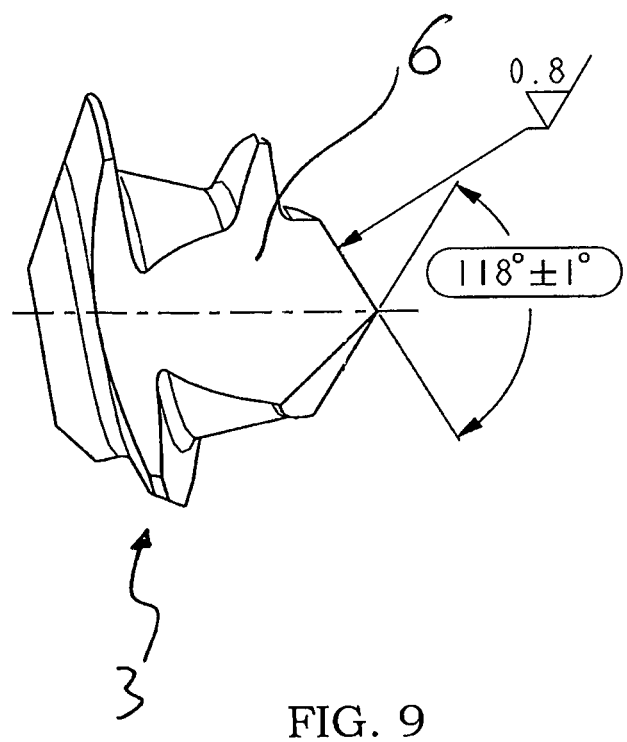

In order to allow easy and correct engagement of the tip with the cortical bone, the tip of the threaded conical end 3 has a cutaway portion, i.e. undercut 6, as can be clearly seen in FIGS. 8 and 9.

Basically, the first part of the thread (on the tipped end) is eliminated by the undercut 6 on the tip so that the tip operates as a centring punch for the first tenths of a millimetre. The harder (outer) part of the cortical bone is thus removed, allowing engagement of the thread.

To conclude, the elongated pin of the present invention has:
- a ratio between the length of the threaded conical end portion 3 of the stem and the diameter d of the stem ranging between 0.8 and 1.2 and preferably between 1 and 1.2, and more preferably equal to 1;
- a ratio between the length of the cylindrical threaded end area 4 of the stem 2 and the diameter d of the stem ranging between 0.8 and 1.25 and preferably between 1 and 1.2, and more preferably equal to 1.1.

Owing to the particular configuration shown, the elongated pin 1 according to the present invention may be fixed onto the cortical bone without entering into the medullary cavity, thus reducing the risks of infection.

Moreover, also owing to the thread on the area 4 of the stem 2 close to the conical tipped end 3, the pin 1 is able to ensure a good grip also on the spongy bone even if there is no cortical bone of suitable thickness.

As can be understood from the above description, the elongated pin according to the present invention is able to meet the requirements and overcome the drawbacks mentioned above in the introductory part of the present description with reference to the prior art.

Obviously a person skilled in the art, in order to satisfy any specific requirements which might arise, may make numerous modifications and variations to the invention described above, all of which are contained moreover within the scope of protection of the invention, as defined by the following claims.

The invention claimed is:

1. An elongated pin for
   an external fixator for temporary and/or permanent fixation applications to treat bone fractures and to connect two or more bone fragments to each other, comprising:
   an elongated cylindrical stem extending along a longitudinal axis (X),
   the elongated cylindrical stem further comprising:
      a cylindrical end area comprising an external thread; and
      a thread-free area extending along most of the length of the elongated cylindrical stem; and
   a conical end portion extending adjacent to the cylindrical end area of the elongated cylindrical stem, the conical end portion comprising a tip and an external thread for inserting the elongated pin into a bone,
   wherein the conical end portion comprising the tip has an overall length, measured along the longitudinal axis (X), equal to the diameter (d) of the elongated cylindrical stem ±20% of the diameter (d), and
   wherein the threaded cylindrical end area of the elongated cylindrical stem has a length, measured along the longitudinal axis (X), equal to the diameter (d) of the elongated cylindrical stem ±25% of the diameter (d).

2. The elongated pin according to claim 1, wherein the conical end portion comprising the tip extends over a total length, measured along the longitudinal axis, equal to the diameter (d) of the elongated cylindrical stem ±10% of the diameter (d).

3. The elongated pin according to claim 2, wherein a ratio between the total length of the threaded conical end portion and the diameter (d) of the elongated cylindrical stem is between 1 and 1.2.

4. The elongated pin according to claim 1, wherein a ratio between a length of the threaded cylindrical end area of the elongated cylindrical stem and the diameter (d) of the elongated cylindrical stem is between 1 and 1.25.

5. The elongated pin according to claim 1, wherein the conical end portion is self-drilling and self-tapping.

6. The elongated pin according to claim 1, wherein the external thread on the conical end portion and the external thread on the cylindrical end area of the elongated cylindrical stem are continuous without interruptions.

7. The elongated pin according to claim 1, wherein the diameter (d) of the elongated cylindrical stem of the elongated pin is between 3 and 6 mm.

8. The elongated pin according to claim 1, wherein the elongated cylindrical stem comprises an end, opposite to the conical end portion comprising the tip, shaped so that it may be coupled in a removable manner with a screwing tool.

9. The elongated pin according to claim 1, wherein the tip of the threaded conical end portion has a cutaway portion.

* * * * *